US008579970B1

(12) United States Patent
Zadno-Azizi et al.

(10) Patent No.: US 8,579,970 B1
(45) Date of Patent: Nov. 12, 2013

(54) MAGNIFYING INTRAOCULAR LENS (75) Inventors: Gholam-Reza Zadno-Azizi, Fremont, CA (US); Scott Evans, Santa Ana, CA (US); Luis Vargas, Irvine, CA (US); Valdemar Portney, Tustin, CA (US)

(73) Assignee: Visiogen, Inc., Santa Ana, CA (US)

( * ) Notice: Subject to any disclaimer, the term of this patent is extended or adjusted under 35 U.S.C. 154(b) by 1202 days.

(21) Appl. No.: 11/426,888

(22) Filed: Jun. 27, 2006

Related U.S. Application Data (60) Provisional application No. 60/694,216, filed on Jun. 27, 2005.

(51) Int. Cl.
*A61F 2/16* (2006.01)

(52) U.S. Cl.
USPC .................... 623/6.13; 623/6.34; 623/6.37

(58) Field of Classification Search
USPC .............. 623/4.1, 6.11, 6.13, 6.32, 6.34
See application file for complete search history.

(56) References Cited

U.S. PATENT DOCUMENTS

| | | | |
|---|---|---|---|
| 4,074,368 A * | 2/1978 | Levy et al. | 623/6.13 |
| 4,240,163 A | 12/1980 | Galin | |
| 4,637,697 A | 1/1987 | Freeman | |
| 4,655,770 A | 4/1987 | Gupta et al. | |
| 4,704,122 A | 11/1987 | Portnoy | |
| 4,816,031 A | 3/1989 | Pfoff | |
| 4,892,543 A | 1/1990 | Turley | |
| 4,932,971 A | 6/1990 | Kelman | |
| 4,963,148 A | 10/1990 | Sulc et al. | |
| 5,220,359 A | 6/1993 | Roffman | |
| 5,354,335 A | 10/1994 | Lipshitz et al. | |
| 5,391,202 A * | 2/1995 | Lipshitz et al. | 623/6.34 |
| 5,443,506 A | 8/1995 | Garabet | |
| 5,507,806 A | 4/1996 | Blake | |
| 5,562,731 A | 10/1996 | Cumming | |
| 5,674,282 A | 10/1997 | Cumming | |
| 5,725,576 A | 3/1998 | Fedorov et al. | |
| 5,876,442 A | 3/1999 | Lipshitz et al. | |
| 5,928,283 A | 7/1999 | Gross et al. | |
| 5,968,094 A | 10/1999 | Werblin et al. | |
| 6,197,059 B1 | 3/2001 | Cumming | |
| 6,358,280 B1 | 3/2002 | Herrick | |
| 6,387,126 B1 | 5/2002 | Cumming | |
| 6,423,094 B1 | 7/2002 | Sarfarazi | |
| 6,450,642 B1 | 9/2002 | Jethmalani et al. | |
| 6,454,802 B1 | 9/2002 | Bretton et al. | |
| 6,464,725 B2 | 10/2002 | Skotton | |
| 6,488,708 B2 | 12/2002 | Sarfarazi | |
| 6,540,353 B1 | 4/2003 | Dunn | |
| 6,596,026 B1 | 7/2003 | Gross et al. | |

(Continued)

FOREIGN PATENT DOCUMENTS

| | | |
|---|---|---|
| CA | 2435907 | 9/2002 |
| DE | 19501444 | 7/1996 |

(Continued)

*Primary Examiner* — David Isabella
*Assistant Examiner* — Joshua Levine
(74) *Attorney, Agent, or Firm* — Visiogen, Inc.

(57) ABSTRACT

A telescopic intraocular lens system comprises a telescopic optical system comprising an anterior optic interconnected with a posterior optic. The optics are substantially aligned on an optical axis of the optical system. The optics are formed from a soft material and the optics are substantially immovable relative to each other along the optical axis in response to accommodative forces of the type observed in the capsular bag of the human eye.

12 Claims, 10 Drawing Sheets

(56) References Cited

U.S. PATENT DOCUMENTS

| | | |
|---|---|---|
| 6,616,691 B1 | 9/2003 | Tran |
| 6,721,104 B2 | 4/2004 | Schachar et al. |
| 6,884,261 B2 | 4/2005 | Zadno-Azizi et al. |
| 6,884,263 B2 | 4/2005 | Valyunin et al. |
| 6,926,736 B2 | 8/2005 | Peng et al. |
| 6,930,838 B2 | 8/2005 | Schachar |
| 7,001,427 B2 | 2/2006 | Aharoni et al. |
| 7,097,660 B2 | 8/2006 | Portney |
| 7,118,596 B2 | 10/2006 | Zadno-Azizi et al. |
| 7,186,266 B2 | 3/2007 | Peyman |
| 7,188,949 B2 | 3/2007 | Bandhauer et al. |
| 7,192,444 B2 | 3/2007 | Blake et al. |
| 7,238,201 B2 | 7/2007 | Portney et al. |
| 2002/0002404 A1 | 1/2002 | Sarfarazi |
| 2002/0183843 A1 | 12/2002 | Blake et al. |
| 2003/0093149 A1 | 5/2003 | Glazier |
| 2003/0105522 A1 | 6/2003 | Glazier |
| 2003/0130732 A1 | 7/2003 | Sarfarazi |
| 2003/0204255 A1 | 10/2003 | Peng et al. |
| 2004/0034414 A1 | 2/2004 | Aharoni |
| 2004/0082995 A1 | 4/2004 | Woods |
| 2004/0236421 A1 | 11/2004 | Lipshitz et al. |
| 2005/0021137 A1 | 1/2005 | Blake et al. |
| 2005/0099597 A1 | 5/2005 | Sandstedt et al. |
| 2005/0119739 A1 | 6/2005 | Glazier |
| 2005/0234547 A1 | 10/2005 | Nguyen et al. |
| 2005/0267575 A1 | 12/2005 | Nguyen et al. |
| 2005/0288784 A1 | 12/2005 | Peyman |
| 2006/0015180 A1 | 1/2006 | Peyman et al. |
| 2006/0184244 A1 | 8/2006 | Nguyen et al. |
| 2006/0238702 A1 | 10/2006 | Glick et al. |
| 2007/0032866 A1 | 2/2007 | Portney |
| 2007/0106377 A1 | 5/2007 | Smith et al. |
| 2007/0282438 A1 | 12/2007 | Hong et al. |

FOREIGN PATENT DOCUMENTS

| | | |
|---|---|---|
| EP | 0162573 | 11/1985 |
| EP | 0337390 A2 | 10/1989 |
| EP | 0336877 | 10/1993 |
| EP | 0897702 | 2/1999 |
| EP | 1723933 | 11/2006 |
| EP | 1723934 | 11/2006 |
| JP | 02-126847 | 5/1990 |
| WO | WO 00/61036 | 10/2000 |
| WO | WO 01/64136 | 9/2001 |
| WO | WO 03/009051 | 1/2003 |
| WO | WO 03/092552 | 11/2003 |
| WO | WO 2004/000171 | 12/2003 |

* cited by examiner

Title: Dual lens silicone telescope

LENS NOTES:

Notes...

GENERAL LENS DATA:

```
Surfaces                   :                        8
Stop                       :                        6
System Aperture            : Entrance Pupil Diameter = 3.4
Glass Catalogs             : SCHOTT MISC OPTOM
Ray Aiming                 : Real Reference, Cache On
  X Pupil shift            :                        0
  Y Pupil shift            :                        0
  Z Pupil shift            :                        0
Apodization                : Uniform, factor =   0.00000E+000
Effective Focal Length     :        20.4861 (in air at system temperature and pressure)
Effective Focal Length     :        27.36943 (in image space)
Back Focal Length          :         0.5277023
Total Track                :              22.65
Image Space F/#            :           6.025323
Paraxial Working F/#       :           6.480023
Working F/#                :           7.38343
Image Space NA             :           0.07703185
Object Space NA            :           0.003342955
Stop Radius                :           0.9818768
Paraxial Image Height      :           5.903478
Paraxial Magnification     :          -0.04332509
Entrance Pupil Diameter    :              3.4
Entrance Pupil Position    :           8.529354
Exit Pupil Diameter        :           1.951972
Exit Pupil Position        :         -15.18534
Field Type                 : Angle in degrees
Maximum Field              :              15
Primary Wave               :           0.55
Lens Units                 : Millimeters
Angular Magnification      :           1.303764

Fields          : 2
Field Type: Angle in degrees
#     X-Value       Y-Value       Weight
1     0.000000      0.000000      0.400000
2     0.000000     15.000000      0.250000

Vignetting Factors
VDX       VDY       VCX       VCY       VAN
1  0.000000  0.000000  0.000000  0.000000  0.000000
2  0.000000  0.000000  0.000000  0.000000  0.000000

Wavelengths     : 1
Units: Microns
#     Value         Weight
1     0.550000      1.000000
```

SURFACE DATA SUMMARY:

| Surf | Type | Comment | Radius | Thickness | Glass | Diameter | Conic |
|---|---|---|---|---|---|---|---|
| OBJ | STANDARD | | Infinity | 500 | | 272.5201 | 0 |
| 1 | EVENASPH | | 7.8 | 0.55 | CORNEA | 10 | -1 |
| 2 | STANDARD | | 6.5 | 2.5 | AQUEOUS | 10 | 0 |
| 3 | STANDARD | | Infinity | 0.1 | AQUEOUS | 10 | 0 |
| 4 | STANDARD | | 1.75 | 1.8 | VG1 | 3.5 | 0 |
| 5 | STANDARD | | -4 | 2.5 | AQUEOUS | 3.5 | 0 |
| STO | STANDARD | | -1.5 | 0.2 | VG1 | 3.5 | 0.8896008 |
| 7 | STANDARD | | 2.242968 | 15 | VITREOUS | 3.5 | -14.43757 |
| IMA | STANDARD | | -12 | | VITREOUS | 11.48511 | 0 |

FIG. 10

Title: Silicone multi lens system with air

LENS NOTES:

Notes...

GENERAL LENS DATA:

```
Surfaces                   :              16
Stop                       :               3
System Aperture            : Entrance Pupil Diameter = 3.5
Glass Catalogs             : SCHOTT MISC OPTOM
Ray Aiming                 : Real Reference, Cache On
  X Pupil shift            :               0
  Y Pupil shift            :               0
  Z Pupil shift            :               0
Apodization                : Uniform, factor =   0.00000E+000
Effective Focal Length     :        31.49792 (in air at system temperature and pressure)
Effective Focal Length     :        42.08122 (in image space)
Back Focal Length          :      -0.1186098
Total Track                :           23.25
Image Space F/#            :        8.999404
Paraxial Working F/#       :        8.999404
Working F/#                :        10.69775
Image Space NA             :      0.05551125
Object Space NA            :       1.75e-010
Stop Radius                :        1.547164
Paraxial Image Height      :        8.439841
Paraxial Magnification     :               0
Entrance Pupil Diameter    :             3.5
Entrance Pupil Position    :        3.037587
Exit Pupil Diameter        :        1.498151
Exit Pupil Position        :       -18.13119
Field Type                 : Angle in degrees
Maximum Field              :              15
Primary Wave               :            0.55
Lens Units                 : Millimeters
Angular Magnification      :        1.748662

Fields         : 2
Field Type: Angle in degrees
#        X-Value         Y-Value         Weight
1        0.000000        0.000000        1.000000
2        0.000000       15.000000        0.100000

Vignetting Factors
VDX       VDY       VCX       VCY       VAN
1  0.000000  0.000000  0.000000  0.000000  0.000000
2  0.000000  0.000000  0.000000  0.000000  0.000000

Wavelengths    : 1
Units: Microns
#       Value           Weight
1      0.550000        1.000000
```

SURFACE DATA SUMMARY:

| Surf | Type     | Comment | Radius    | Thickness | Glass    | Diameter | Conic    |
|------|----------|---------|-----------|-----------|----------|----------|----------|
| OBJ  | STANDARD |         | Infinity  | Infinity  |          | 0        | 0        |
| 1    | EVENASPH |         | 7.8       | 0.55      | CORNEA   | 10       | -1       |
| 2    | STANDARD |         | 6.5       | 3.05      | AQUEOUS  | 10       | 0        |
| STO  | STANDARD |         | Infinity  | 0.2       | AQUEOUS  | 10       | 0        |
| 4    | EVENASPH |         | 5         | 0.4       | VG1      | 4        | -11.7031 |
| 5    | STANDARD |         | -6.959677 | 0.05      |          | 4        | 0        |
| 6    | STANDARD |         | 5.5       | 0.6       | VG1      | 4        | 0        |
| 7    | STANDARD |         | -6.2      | 0.05      |          | 4        | 0        |
| 8    | STANDARD |         | 5         | 0.4       | VG1      | 3        | 0        |
| 9    | STANDARD |         | Infinity  | 0         | AQUEOUS  | 3.144392 | 0        |
| 10   | STANDARD |         | Infinity  | 0.4       | VG1      | 3.144392 | 0        |
| 11   | STANDARD |         | 3.2       | 0.65      |          | 3        | 0        |
| 12   | STANDARD |         | -3.2      | 0.05      | VG1      | 3        | 0        |
| 13   | STANDARD |         | 3.2       | 0.65      |          | 3        | 0        |
| 14   | STANDARD |         | -2.9      | 0.2       | VG1      | 3        | 0        |
| 15   | EVENASPH |         | 3.391167  | 16        | VITREOUS | 3        | 1        |
| IMA  | STANDARD |         | -12       |           | VITREOUS | 22.38625 | 0        |

FIG. 11

MAGNIFYING INTRAOCULAR LENS

RELATED APPLICATIONS

This application claims the benefit under 35 U.S.C. §119 (e) of U.S. Provisional Application No. 60/694,216, filed Jun. 27, 2005, titled MAGNIFYING INTRAOCULAR LENS. The entire contents of the above-mentioned provisional application are hereby incorporated by reference herein and made a part of this specification.

BACKGROUND

1. Field

Certain embodiments disclosed herein relate to telescopic intraocular lenses, methods for treatment of macular degeneration with telescopic intraocular lenses, and methods and apparatus for compacting and injecting telescopic intraocular lenses.

2. Description of the Related Art

Age-related macular degeneration, or AMD, is a disease that affects the retina which contains an array of cells that line the back of the eye. The light falling onto these cells in the retina is transformed into electrical signals which are transmitted to the brain centers that process and interpret them. The most concentrated collection of photosensitive cells in the retina, including those that enable critical color and fine detail vision, are found in the Bulls-Eye center zone in an area called the macula. Macular degeneration is the name given to that group of diseases that causes sight-sensing cells in the macular zone of the retina to malfunction or lose function and results in debilitating loss of vital central or detail vision. The brain learns to compensate and fill in the missing part of the picture in early cases with spotty macular cell damage or dysfunction, so most people only present to their ophthalmologist when disease is fairly advanced. Telescopic intraocular lenses are often prescribed for patients suffering from AMD.

SUMMARY

Certain embodiments described herein comprise a device or lens system designed to treat macular degeneration. The lens system can comprise an implant that can be inserted into the eye by a physician. The lens system preferably magnifies the visual image that is projected onto the retina in the visual field. The lens system also is designed to be inserted through a handheld injector and as such can be compressible and flexible enough to be folded and injected through a small diameter nozzle. Certain embodiments of the lens system combine the benefits of silicone material (flexibility, compressibility, ease of manufacture) with a dual lens magnification configuration.

Certain embodiments of the lens system described herein can be sized to be placed into the posterior chamber of the eye only and have an overall length of 4 mm. The lens system can be constructed using flexible polymers that allow the system to be compressed and folded so that the system can be injected into the posterior chamber using syringe like injectors common in the field. The lens system can comprise a multi-lens system to provide equivalent magnification compared to other systems but with the potential for easier insertion, smaller incisions, reduced trauma to the eye after insertion, and without introducing cylinder and spherical refractive error.

The device can comprise a dual optic lens system with several significant modifications to enable the lens to magnify the image. The anterior and the posterior optics preferably have large powers and utilize maximal separation between optics to increase the magnification potential. The optics are not designed to move relative to each other after the optics are implanted and in fact movement of the optics should preferably be restricted because the high powers create refractive errors such as high spherical aberrations that are detrimental to vision quality.

The various embodiments of the lens system discussed herein may use connector members (such as a haptic system) to couple the anterior optic to the posterior optic. This feature facilitates sequential insertion through an injector by keeping the two optics connected together and also assists in maintaining a proper optical alignment after insertion. The various disclosed embodiments of the lens system may utilize a retention feature to maintain a consistent position of the lens system inside the capsular bag. This feature can be helpful to ensure that the lens system is positioned correctly in a stable secure position in the capsular bag. The lens system can also have an attachment feature (connector member(s) or pin(s)) to secure the two lenses together to minimize movement of the lenses relative to each other. This limitation of movement can be helpful to reduce the impact of potential spherical aberration in the system due to high powered optics.

In one embodiment, a telescopic intraocular lens system comprises a telescopic optical system comprising an anterior optic interconnected with a posterior optic. The optics are substantially aligned on an optical axis of the optical system. The optics are formed from a soft material and the optics are substantially immovable relative to each other along the optical axis in response to accommodative forces of the type observed in the capsular bag of the human eye.

In one variation of this embodiment, the optical system comprises at least one gas lens element and at least non-gas lens element. In one variation, the anterior optic comprises at least one biconvex gas lens, and the posterior optic can optionally comprise at least one biconcave gas lens. In one variation, the soft material comprises silicone. One embodiment comprises a method of treating macular degeneration; the method comprises implanting the lens system into the capsular bag of an eye of a patient.

In another embodiment, a telescopic intraocular lens system comprises a telescopic optical system comprising at least one gas lens element and at least non-gas lens element. The lens elements are substantially aligned on an optical axis of the optical system. The optical system is sized to fit substantially within the capsular bag of the human eye.

In one variation of this embodiment, the optical system is 3 mm-6 mm long, as measured along the optical axis. In one variation, the at least one non-gas lens element is formed from a soft material. In one variation, the optical system, other than the at least one gas lens element, is formed from a soft material. In one variation, the optical system comprises at least one pair of biconvex gas lenses, and can optionally further comprise at least one pair of biconcave gas lenses posterior of the biconvex gas lenses. One embodiment comprises a method of treating macular degeneration; the method comprises implanting the lens system into the capsular bag of an eye of a patient.

Another embodiment comprises a method of preparing for subsequent insertion a telescopic intraocular lens system having multiple interconnected optics. The method comprises compacting the optics of the telescopic intraocular lens system while the optics remain interconnected.

In one variation of this embodiment, compacting comprises compacting in an injector. In one variation, the method further comprises advancing the compacted lens system distally within a nozzle of the injector with one of the optics disposed in front of the other of the optics. In one variation, compacting comprises folding. In one variation, the method further comprises sequentially inserting the optics into an eye.

In another embodiment, an intraocular lens injector comprises an injector nozzle which extends along a longitudinal axis thereof. The injector nozzle has a nozzle lumen with a distal terminal portion having a lumen cross-sectional area measured in a plane orthogonal to the longitudinal axis. The injector further comprises a telescopic intraocular lens system disposed in the injector. The lens system has an optical axis when in an unstressed condition. The lens system comprises at least one optic having an optic cross-sectional area measured in a plane orthogonal to the optical axis. The lumen cross-sectional area is smaller than the optic cross-sectional area.

In one variation of this embodiment, the at least one optic is formed from a soft material. In one variation, the at least one optic includes at least one air lens element. In one variation, the injector further comprises a lens compactor, and the telescopic intraocular lens system is disposed in the lens compactor. In one variation, the telescopic intraocular lens system comprises a first optic interconnected with a second optic. In one variation, the second optic has a second optic cross-section measured in a plane orthogonal to the optical axis, and the lumen cross-sectional area is smaller than the second optic cross-sectional area.

Certain objects and advantages of the invention are described herein. Of course, it is to be understood that not necessarily all such objects or advantages may be achieved in accordance with any particular embodiment of the invention (s). Thus, for example, those skilled in the art will recognize that the invention(s) may be embodied or carried out in a manner that achieves or optimizes one advantage or group of advantages as taught herein without necessarily achieving other objects or advantages as may be taught or suggested herein.

The embodiments summarized above are intended to be within the scope of the invention(s) herein disclosed. However, despite the foregoing discussion of certain embodiments, only the appended claims (and not the present summary) are intended to define the invention(s). The summarized embodiments, and other embodiments of the present invention(s), will become readily apparent to those skilled in the art from the following detailed description of the preferred embodiments having reference to the attached figures, the invention(s) not being limited to any particular embodiment(s) disclosed.

BRIEF DESCRIPTION OF THE DRAWINGS

FIG. 10 is a table showing optical calculations and data for one embodiment of the optical system of FIG. 3.
FIG. 11 is a table showing optical calculations and data for one embodiment of the optical system of FIG. 4.

DETAILED DESCRIPTION OF THE PREFERRED EMBODIMENTS

Figure 1:
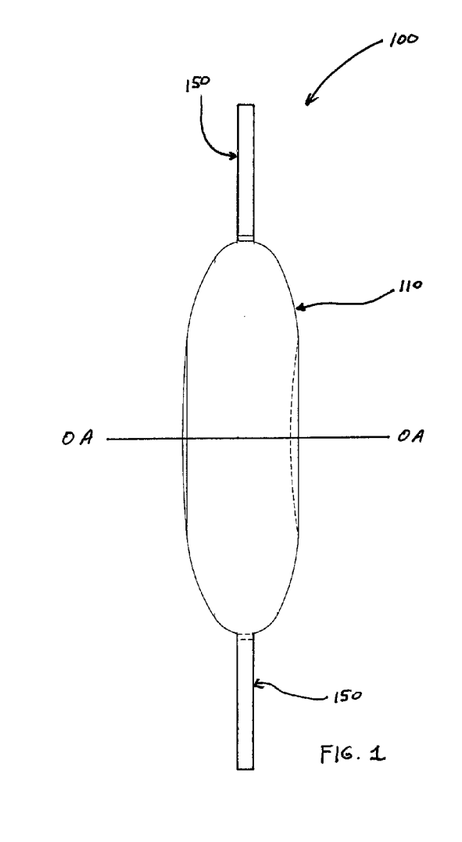
FIG. 1 is a side view of a telescopic intraocular lens system.
Figure 2:
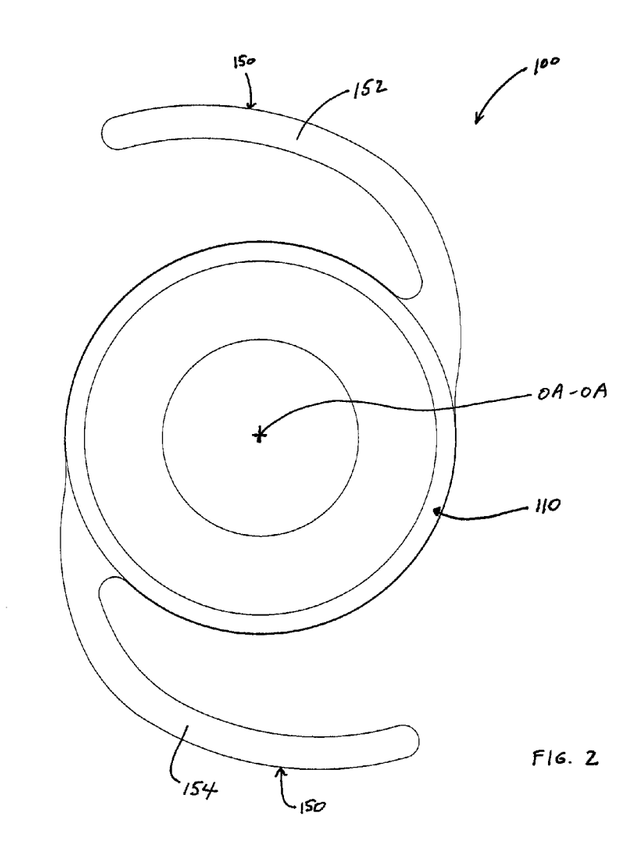
FIG. 2 is a front view of the lens system of FIG. 1.

FIGS. 1-2 depict schematically one embodiment of a telescopic intraocular lens system 100. The lens system 100 generally comprises a telescopic optical system 110 and a haptic system 150 which extends radially outwardly from the optical system 110. The telescopic optical system 110, several embodiments of which are discussed in further detail below, has an optical axis OA-OA which is generally coincident with the optical axis of the eye (not shown) upon implantation of the lens system 100.

The depicted haptic system 150 includes two opposed cantilever-spring haptics 152, 154, but more than two such haptics can be employed in other embodiments. Alternatively, other haptic types, such as plate haptics or radially outward extensions of the optical system 110 may be employed in place of the depicted spring haptics 152, 154. The haptic system 150 preferably keeps the optical system 110 substantially centered in its implant location, which can be in the capsular bag, sulcus, or in any other suitable location in the eye. Preferably, the haptics 152, 154, when implemented as cantilever springs as shown, spread to an overall width of about 13 mm when unconstrained, as the lens system 100 is viewed along the optical axis OA-OA.

Figure 3:
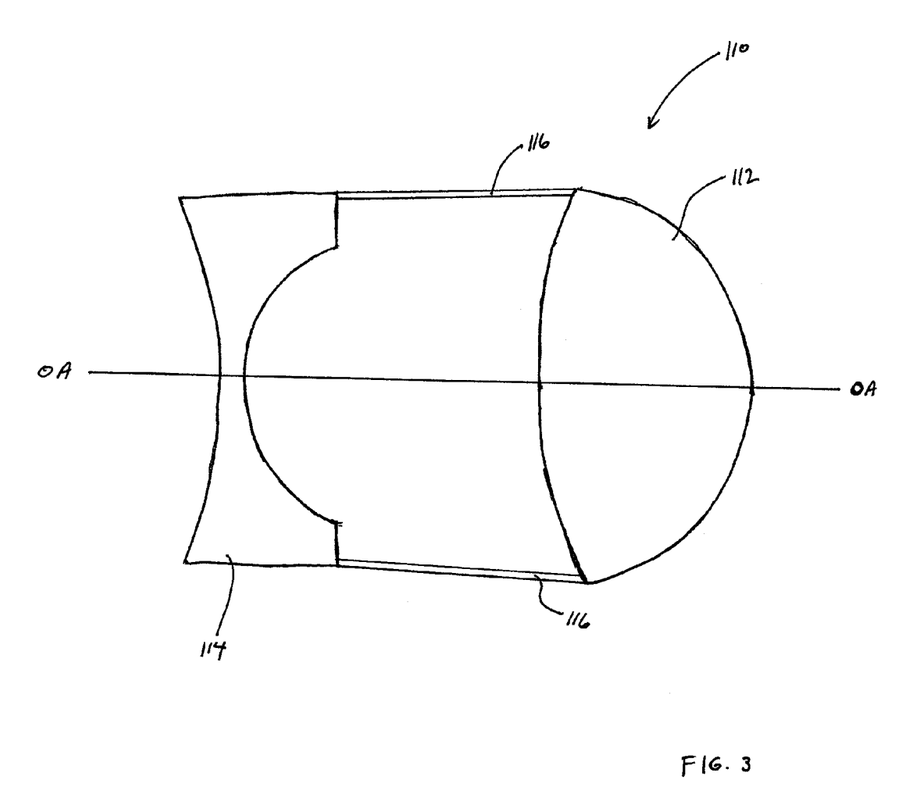
FIG. 3 is a side view of one embodiment of a telescopic optical system for use in the lens system of FIG. 1.

FIG. 3 depicts one embodiment of the telescopic optical system 110, which generally comprises an anterior optic 112 connected to a posterior optic 114, both of which are preferably formed from a soft, flexible optical material such as silicone; soft or foldable acrylics; silicone-acrylic blends; block copolymers of styrene-ethylene-butylene-styrene (C-FLEX) or other styrene-base copolymers; polyvinyl alcohol (PVA); polyurethanes; or any other suitable flexible optical polymer. As used in the present disclosure to refer to materials for the optics of the optical system 110, "soft" refers to a material which, when formed into an implantable optic, is sufficiently pliable to permit compression, compaction and/or folding of the resulting optic with the fingertips, with forceps and/or with standard intraocular lens injectors.

The optics 112, 114 are interconnected with one or more connector members 116. The connector members 116 can comprise individual ribs or arms, or they can comprise a cylinder that joins the perimeter of the posterior face of the anterior optic 112 to the perimeter of the anterior face of the posterior optic 114. This cylinder may be formed with openings therein to permit aqueous fluid flow between the optics 112, 114.

Preferably, the connector member(s) 116 maintain the optics 112, 114 at a fixed separation distance which is selected to provide a desired optical or magnification power of the optical system 110. Thus the connector member(s) 116 should have sufficient column strength to prevent the optics 112, 114 from moving together under the typical accommodative forces observed in the capsular bag, and to prevent the optics 112, 114 from converging when implanted in the bag. The connector member(s) 116 advantageously also serve to prevent separation of the optics 112, 114 when the optical system 110 is in use. By resisting relative movement of the optics 112, 114 in both directions along the optical axis OA-OA, the connector members 116 keep the optics 112, 114 in a fixed position relative to each other, and substantially immovable relative to each other along the optical axis. When the lens system 100 is implanted, the optical power of the optical system 110 does not change substantially in response to the accommodative movement of the ciliary muscle.

Alternatively, the connector members 116 can be configured to permit a small relative movement of the optics 112, 114 along the optical axis OA-OA, to permit some accommodation and/or focus correction. This can be facilitated with connector members 116 that are sufficiently elastic or spring-like in response to compressive forces (e.g. accommodative forces developed by the eye or capsular bag) acting on the optics 112, 114. Optionally, one or more stop members (not shown) which extend generally parallel to, and are more rigid than, the connector members 116 can be employed to set a lower limit on the distance between the optics 112, 114, and stop convergence of the optics 112, 114 beyond this lower limit.

The optics 112, 114 form a telescopic optical system that provides a magnified image, preferably by 30% or more (i.e., providing a magnified image at 130% or more of its actual size). In one embodiment, the anterior optic 112 is a high-power (e.g., +77 diopters or more) positive optic and the posterior optic 114 is a high-power (e.g., −107 diopters or more) negative optic. (The specified powers are measured with the optics in question immersed in water.) In one variation of this embodiment, the anterior optic 112 is high power positive biconvex optic with a refractive index of 1.433, center thickness of 1.8 mm, a 1.75 mm front radius and −4.0 mm back radius; and the posterior optic 114 is a high negative power biconcave optic with a refractive index of 1.433, center thickness of 0.2 mm, a −1.5 mm front radius and 2.24 mm back radius. The configuration of the optics 112, 114 may permit aqueous fluid to flow between the optics 112, 114. In some embodiments, one or both of the optics 112, 114 includes at least one aspheric optical surface.

The high powers and/or intra-lens spacing of the various embodiments of the optical system 110 shown in FIG. 3 facilitate a telescopic system that can be manufactured to fit within the capsular bag, or substantially within the capsular bag (projecting anteriorly through a capsulorhexis by no more than about 1-2 mm). In various embodiments, the optical system 110 of FIG. 3 can be less than 6 mm, or less than 5 mm, or 4 mm-6 mm, or about 4 mm in length, as measured along the optical axis OA-OA. Preferably, the optics 112, 114 of the optical system 110 of FIG. 3 are about 6 mm in diameter, but this size is not critical and can be varied somewhat.

Figure 4:
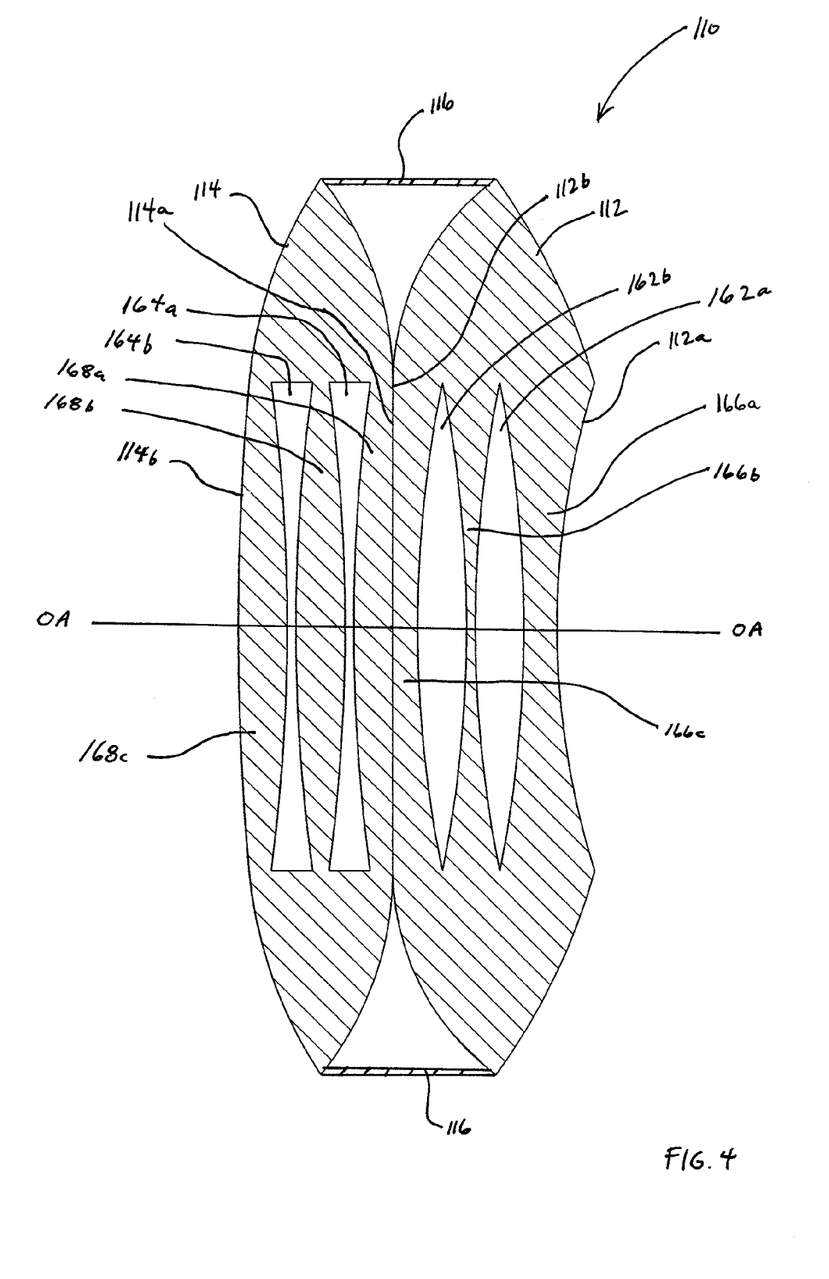
FIG. 4 is a side sectional view of one embodiment of a telescopic optical system for use in the lens system of FIG. 1.

FIG. 4 depicts additional embodiments of the telescopic optical system 110, which can be similar to the optical system 110 of FIG. 3, except as further described below. In the optical system 110 of FIG. 4, one or both of the anterior and posterior optics 112, 114 is formed from a soft optical material (e.g. silicone, or any of the other soft, flexible optical materials identified above), and preferably includes at least one gas lens element and at least one non-gas lens element disposed therein.

In the depicted embodiment, the anterior optic 112 is a soft optic with a concave anterior surface 112a and a plano posterior surface 112b, and a pair of anterior biconvex gas lens elements 162a, 162b; and the posterior optic 114 is a soft optic with a plano anterior surface 114a, a plano or slightly convex posterior surface 114b, and a pair of posterior biconcave gas lens elements 164a, 164b. Non-gas lens elements 166 are formed in the depicted embodiment of the anterior optic 112, including a biconcave lens element 166a formed between the concave anterior surface 112a of the optic 112, and the anterior biconvex gas lens element 162a; a biconcave lens element 166b formed between the biconvex gas lens elements 162a, 162b; and a concave-plano lens element 166c formed between the posterior biconvex gas lens element 162b and the plano posterior surface 112b of the anterior optic 112. Non-gas lens elements 168 are formed in the depicted embodiment of the posterior optic 114, including a plano-convex lens element 168a formed between the plano anterior surface 114a of the optic 114, and the anterior biconcave gas lens element 164a; a biconvex lens element 168b formed between the biconcave gas lens elements 164a, 164b; and a biconvex lens element 168c formed between the posterior biconcave gas lens element 164b and the convex posterior surface 114b of the posterior optic 112. Of course, the lens elements depicted in FIG. 4 represent only a preferred arrangement, and the number and type of gas lens element(s) and non-gas lens element(s) can be varied in further embodiments of the optical system 110 of FIG. 4. (The same is true of the further embodiments of the optical system 110 shown in FIGS. 5-8 and discussed in further detail below.)

In the depicted embodiment, the anterior optic 112 has a high positive power (e.g., +300 diopters or more) and the posterior optic 114 has a high negative power (e.g., −670 diopters or more). The specified powers are measured with the optics in question immersed in water.

The gas lens(es) take advantage of the difference in refractive index between gases and optical polymers such as silicone, to provide high magnification (e.g., 200% or more) without requiring an unduly long or thick optical system 110. Thus, the various embodiments of the optical system 110 shown in FIG. 4 can be manufactured to fit within the capsular bag, or substantially within the capsular bag (projecting anteriorly through a capsulorhexis by no more than about 1-2 mm). In various embodiments, the optical system 110 of FIG. 4 can be less than 6 mm, or less than 5 mm, 3 mm-6 mm, 3 mm-5 mm, or about 4 mm in length, as measured along the optical axis OA-OA. Preferably, the lens elements 162, 164, 166, 168 of the optical system 110 of FIG. 4 are about 6 mm in diameter, and the optics 112, 114 are about 9-11 mm in diameter, but these sizes are not critical and can be varied somewhat.

The connector members 116 can be generally similar to the connector members 116 of FIG. 3, and serve to hold the two optics 112, 114 together in the lens system 100. Instead of or in addition to the connector members 116, the abutting surfaces 112b, 114a of the optics 112, 114 can be adhered together with adhesives, heat bonding, self-adhesion, mechanical connections, etc. to secure the optics 112, 114 together. Advantageously, the abutting relation of the surfaces 112b, 114a helps to keep the optics 112, 114 in a fixed position relative to each other, by preventing convergence of the optics 112, 114. The connector members 116 (and, where employed, the adhesion or self-adhesion of the surfaces 112b, 114a to each other) preferably also prevent separation of the optics 112, 114 and thereby assist in maintaining the optics 112, 114 in a fixed position relative to each other.

In some embodiments, the gas that fills the gas lenses 162a, 162b, 164a, 164b is air. However, in other embodiments a heavier-molecule gas such as carbon dioxide or argon can be employed to minimize gas leakage from the optics 112, 114. Whichever gas is employed, the inner walls defining the gas lenses can be coated, in some embodiments, with a low-gas-permeable coating to reduce gas leakage.

Figure 5:
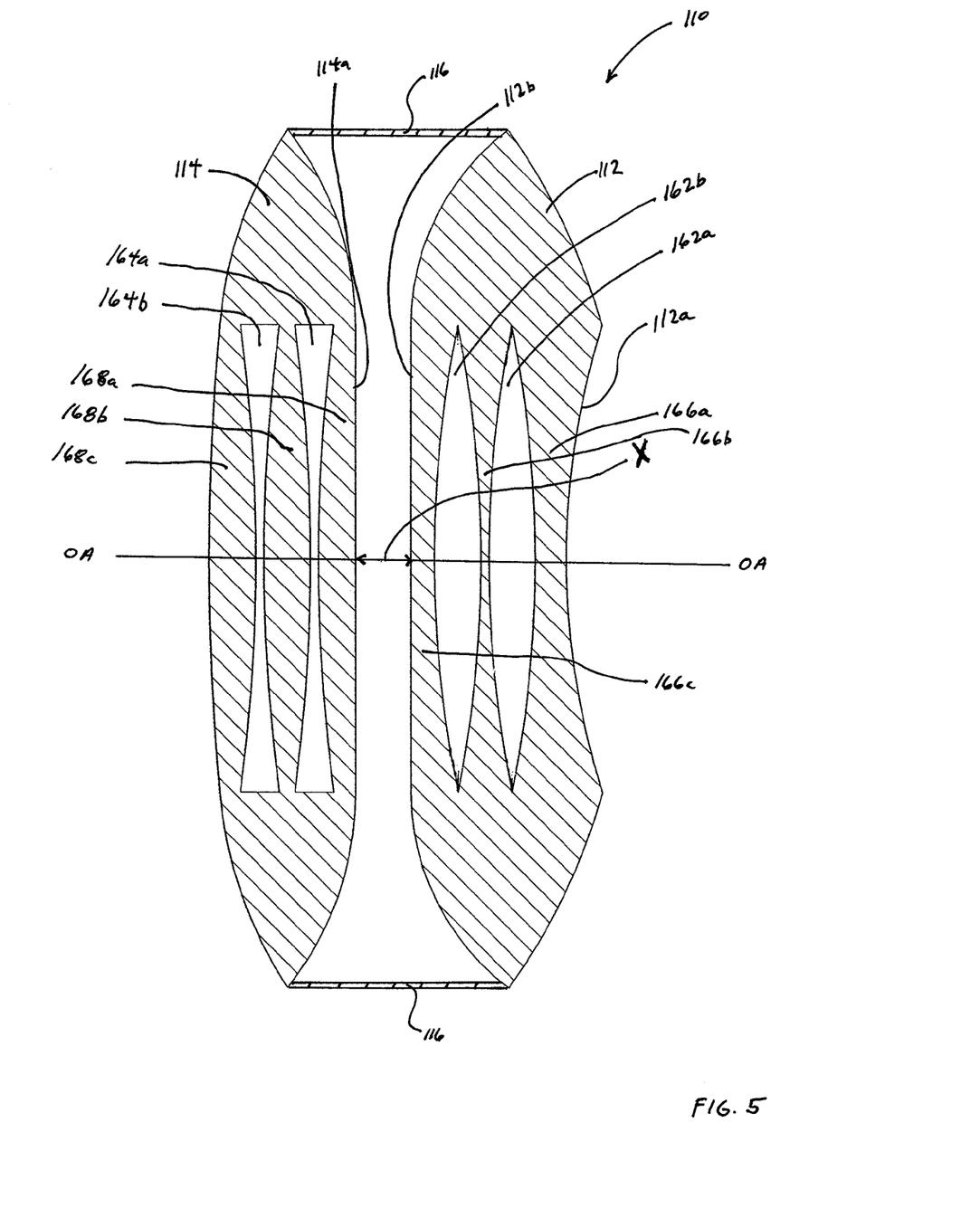
FIG. 5 is a side sectional view of one embodiment of a telescopic optical system for use in the lens system of FIG. 1.

FIG. 5 depicts further embodiments of the telescopic optical system 110, which can be similar to the optical systems 110 of FIGS. 3 and 4, except as further described below. In particular, the depicted embodiment of the optical system 110 of FIG. 5 is similar to that of FIG. 4, with the exception that the optics 112, 114 (particularly the surfaces 112b, 114a thereof) are separated by a separation distance X along the optical axis OA-OA, by virtue of the relatively longer connection member(s) 116. Preferably, the connector member(s) 116 have sufficient column and tensile strength to prevent relative motion of the optics 112, 114 along the optical axis OA-OA and maintain the optics 112, 114 substantially at the separation distance X when the optical system 110 is in use in the eye. In comparison to the embodiment of FIG. 4, the separation distance X between the optics promotes a higher magnification power for the telescopic optical system 110 of FIG. 5.

Figure 6:
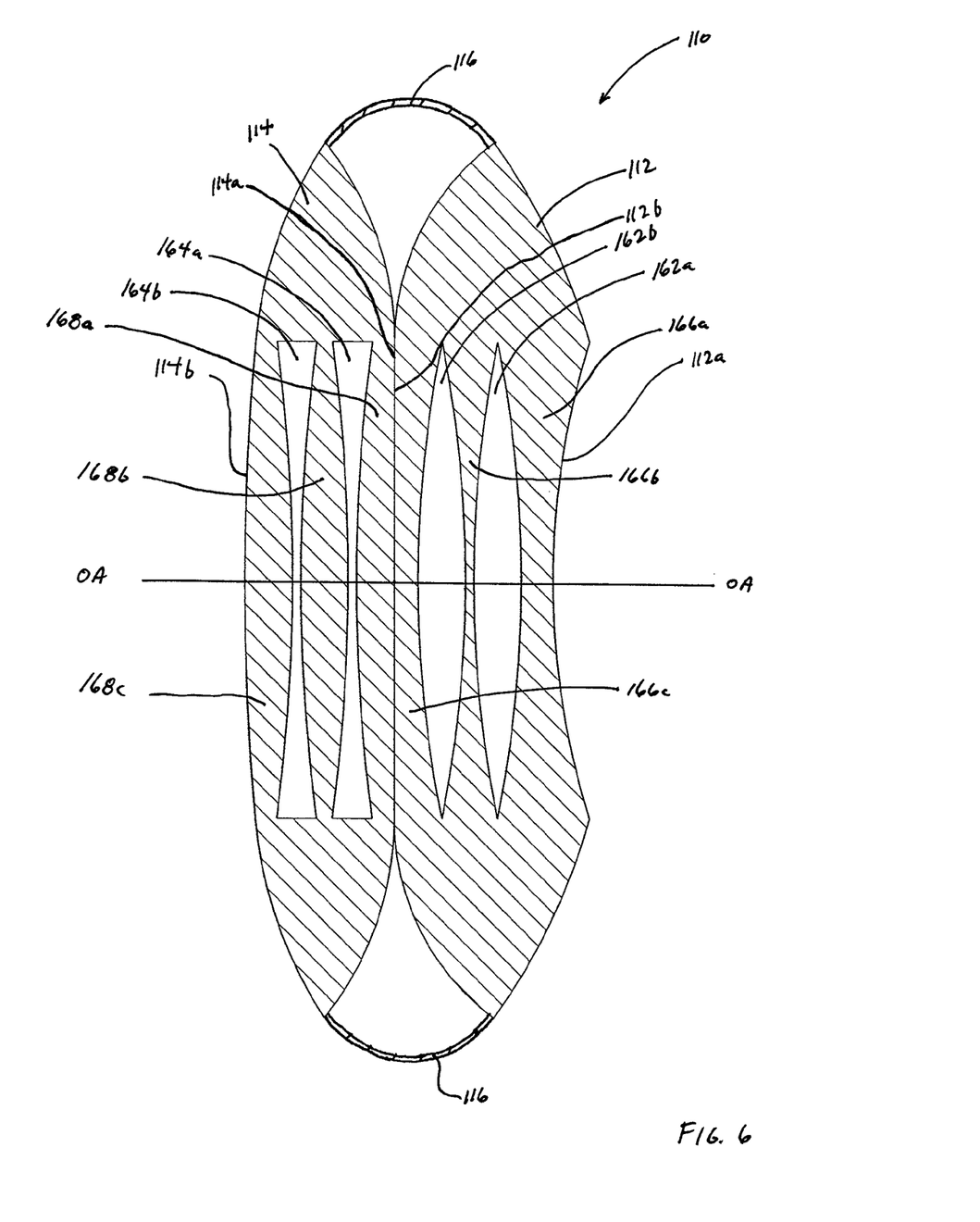
FIG. 6 is a side sectional view of one embodiment of a telescopic optical system for use in the lens system of FIG. 1.
Figure 7:
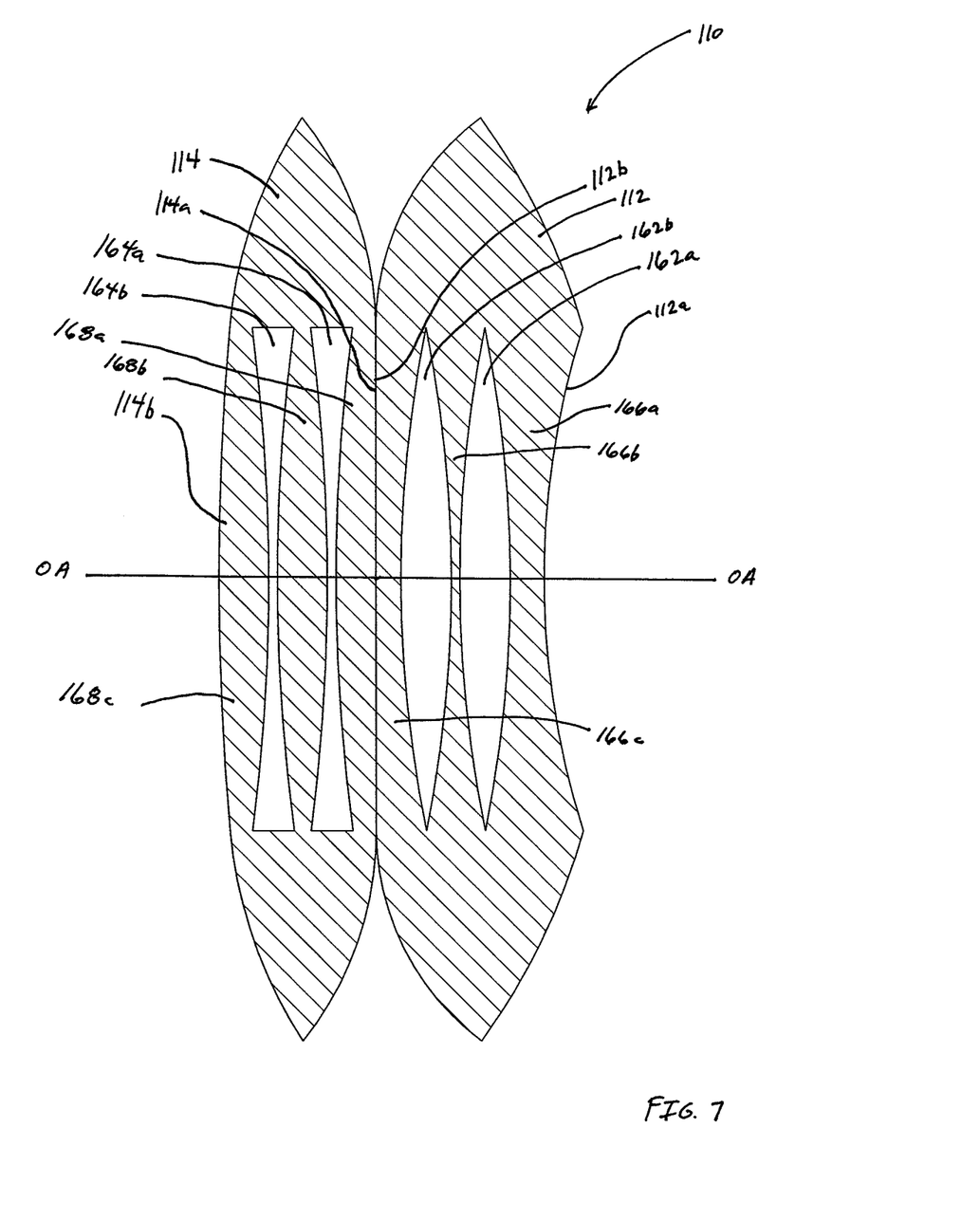
FIG. 7 is a side sectional view of one embodiment of a telescopic optical system for use in the lens system of FIG. 1.

FIGS. 6 and 7 depict further embodiments of the telescopic optical system 110, which can be similar to the embodiments of FIGS. 4 and 5, except as further discussed below. FIG. 6 depicts an embodiment which is similar to that of FIG. 4, except that the connector members 116 have an arcuate shape as depicted. The connector members advantageously provide an overall shape for the optical system which conforms well to the inside of the capsular bag. Thus, in one variation, the optical system 110 is sized to serve as a bag-filling implant, wherein the connector members 116 are sized to extend to the equator of the bag. In this variation, the connector members 116 effectively serve as haptics.

The embodiment of FIG. 7 is similar to the embodiments of FIGS. 4, 5 and 6, with the exception that the connector members 116 are omitted, and the optics 112, 114 are adhered to each other at the surfaces 112b, 114a, or simply abut without adhesion, in which case the optics 112, 114 can be inserted into the capsular bag adjacent one another, with the radially outer portions of the optics 112, 114 serving as haptics.

Figure 8:
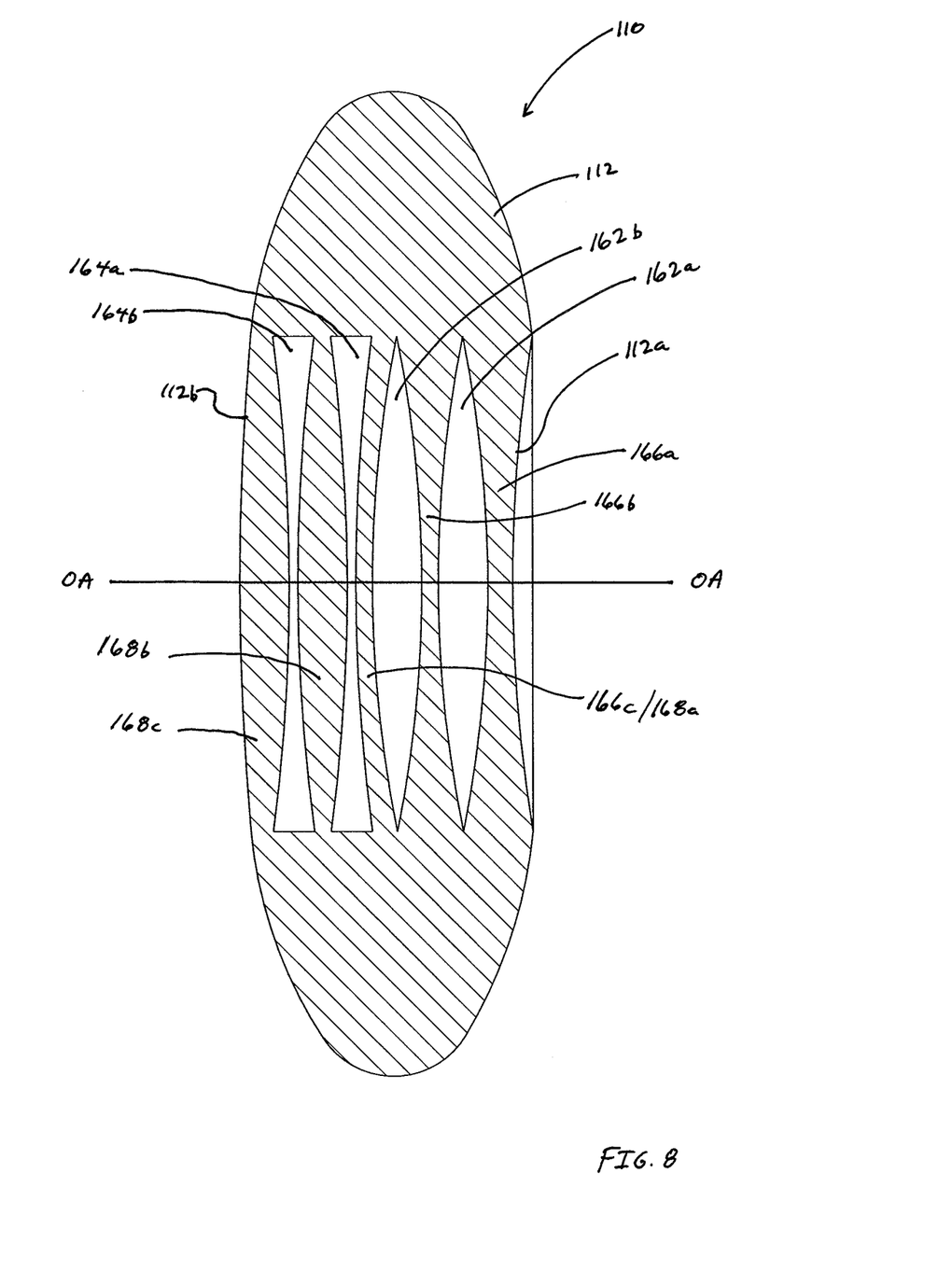
FIG. 8 is a side sectional view of one embodiment of a telescopic optical system for use in the lens system of FIG. 1.

FIG. 8 depicts further embodiments of the optical system 110 which can be similar to the embodiments of FIGS. 4-7, except as further discussed below. The optical system 110 of FIG. 8 comprises a single, unitary optic 112 in which are disposed both the anterior gas lens elements 162a, 162b and the posterior gas lens elements 164a, 164b. The optical system 110 of FIG. 8 can form part of the intraocular lens system 100 as discussed above, or the optical system 110 of FIG. 8 can comprise a complete implant unto itself, with the optic body filling the volume of the capsular bag and the radially outer portions of the optic 112 serving as haptics.

In any of the embodiments of the optical system 110 described herein, any one or more of the lens elements making up the optical system may comprise a diffractive lens element with one or more diffractive lens surfaces. The use of diffractive lens elements advantageously facilitates thinner optic(s) 112, 114 and a shorter optical system 110, as measured along the optical axis OA-OA.

The softness and compressibility of the various embodiments of the telescopic optical system 110 disclosed herein advantageously facilitate inserting the telescopic lens system 100 into the eye of a patient (e.g. into the capsular bag of the patient's eye) through a small incision, and/or with a lens injector. Accordingly, one embodiment of a method of preparing the telescopic lens system 100 for subsequent insertion involves compacting the lens system, which for a multiple-optic lens system 100 preferably involves compacting the optics of the lens system 100 while the optics remain interconnected. Compacting can involve folding the optics or crushing them, for example, by forcing the optics into a low-profile shape suitable for subsequent insertion. This compacting and/or subsequent insertion can be performed manually, or with a suitable lens injector.

Compacting the lens system 100 can comprise manipulating the anterior and posterior optics 112, 114 to place the lens system 100 in a low-profile condition, in which the viewing elements 112, 114 are out of axial alignment and are preferably situated so that no portion of the anterior optic 112 overlaps any portion of the posterior optic 114, as viewed along the optical axis OA-OA. (Such a low-profile condition is shown in FIG. 39(B) of United States Patent Application No. 2002/0107568 A1, published on Aug. 8, 2002, titled ACCOMMODATING INTRAOCULAR LENS SYSTEM, the entire contents of which are hereby incorporated by reference herein and made a part of this specification.) Thus, manipulating the lens system 100 into the low-profile condition can involve displacing the optics 112, 114 relative to each other in a direction transverse or orthogonal to the optical axis OA-OA of the unstressed lens system 100. In the low-profile condition, the thickness of the lens system 100 is minimized because the optics 112, 114 are not "stacked" on top of each other, but instead have a side-by-side configuration. From the low-profile condition the optics 112, 114 and/or other portions of the lens system 100 can be folded or rolled generally about an axis orthogonal to the optical axis and passing through both optics. Upon folding/rolling, the lens system 100 can be placed in an injector lumen and inserted into the eye.

Figure 9:
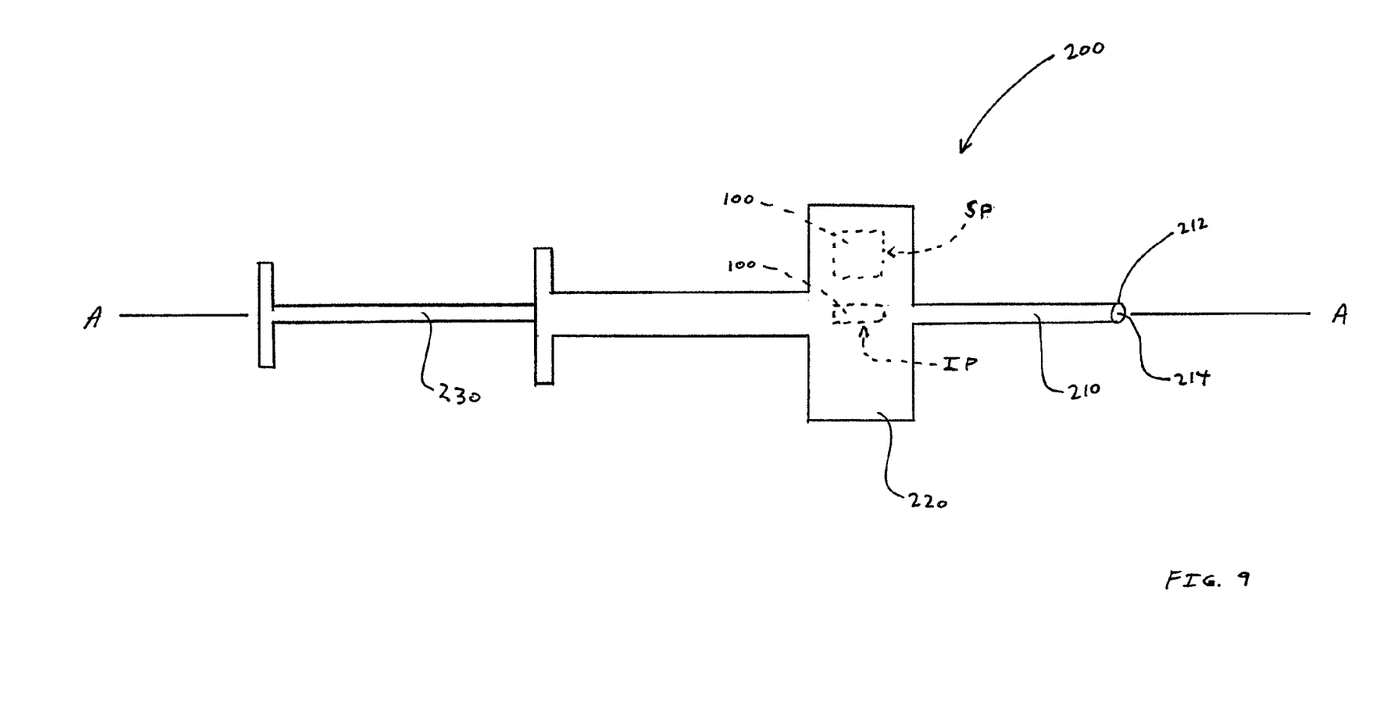
FIG. 9 is a schematic view of an injector for use in implanting the lens system of FIG. 1.

The lens system 100 can be injected into an eye of a patient with an injector such as the injector 200 shown in FIG. 9. The injector 200 generally comprises an injector nozzle 210 with a distal tip 212 and an inner lumen 214 through which the lens system 100 passes as it is injected into the patient's eye. The injector nozzle 210 and injector lumen 214 preferably extend along an injector axis A-A.

The injector 200 preferably further comprises a lens module 220 which is configured to contain and/or compact the lens system 100 before injection. The lens module 220 can comprise any of a variety of suitable apparatus, loaded with the telescopic lens system 100. Thus the lens module 220 can comprise a detachable box or cartridge which holds or stores the lens system 100 in a storage position SP in a substantially unstressed state, and includes an actuator to force the lens system 100 into a compacted configuration and move it into an injection position IP, aligned with (or situated within) the injector nozzle 210. Alternatively, the lens module 220 can comprise a permanently attached container/compactor which holds or stores the lens system 100 in such a storage position in the unstressed state, with an actuator to compact the lens system 100 and move it into injection position IP. Suitable mechanisms for use as the lens module 220 are shown in U.S. Patent Application Publication No. 20041/0160575 A1, published on Aug. 19, 2004, titled METHOD AND DEVICE FOR COMPACTING AN INTRAOCULAR LENS, the entirety of which is hereby incorporated by reference herein and made a part of this specification. A lens module 220 incorporating the mechanisms of the above-mentioned '575 publication, and/or similar mechanisms, can be used to compact the lens system 100 into a low-profile condition as discussed above and as shown in FIG. 39(B) of the above-mentioned '568 publication. The lens module 220 or injector 200 can so compact the lens system by, e.g., displacing the optics 112, 114 relative to each other in a direction transverse or orthogonal to the optical axis OA-OA of the unstressed lens system 100.

To facilitate insertion of the lens system 100 through a small incision, the nozzle lumen 214 (or at least the distal portion thereof) preferably has a small profile. In particular, the nozzle lumen 214 (or at least the distal portion thereof) preferably has a cross-sectional area, as measured in a plane orthogonal to the injector axis A-A, which is smaller than the cross-sectional area of the optic(s) 112 and/or 114 of the lens system 100, as the lens system 100 is viewed along the optical axis. In another embodiment, the distal portion of the nozzle lumen 214 has a cross-sectional profile, as observed in a plane orthogonal to the injector axis A-A, whose largest dimension (e.g. the diameter of a circular profile or the major axis of an oval or elliptical profile) is smaller than the largest dimension of the profile of the optic(s) 112 and/or 114 of the lens system 100, as the lens system 100 is viewed along the optical axis.

Preferably, the telescopic lens system 100 assumes the cross-sectional profile of (at least the proximal portion of) the injector nozzle 214 when it is compacted into the compacted configuration (shown at position IP). Thus, by distal movement of a plunger 230 of the injector 200, the user can urge the compacted lens system 100 distally down the lumen 214 of the nozzle 210, to the distal tip 212 thereof, and into the patient's eye.

Advantageously, the entire lens system 100 (and/or the entire optical system 110 thereof) may comprise a single piece of material, i.e. one that is formed without need to assemble two or more components by gluing, heat bonding, the use of fasteners or interlocking elements, etc. This characteristic increases the reliability of the lens system 100 or optical system 110 by improving its resistance to material fatigue effects which can arise as the lens system experiences millions of accommodation cycles throughout its service life. The molding process and mold tooling discussed in the above-mentioned '568 publication, lend themselves to the molding of lens systems 100 that comprise a single piece of material. However, any other suitable technique may be employed to manufacture single-piece lens systems.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular embodiments described above, but should be determined only by a fair reading of the claims that follow.

What is claimed is:

1. A telescopic intraocular lens system comprising:
   a telescopic optical system comprising an anterior optic interconnected with a posterior optic, said optics substantially aligned on an optical axis of said optical system;
   wherein said optics are formed from a soft material and said optics are substantially immovable relative to each other along said optical axis in response to accommodative forces of the type observed in the capsular bag of the human eye; and
   wherein said posterior optic comprises at least one biconcave gas lens.

2. The lens system of claim 1, wherein said optical system comprises at least one gas lens element and at least one non-gas lens element.

3. The lens system of claim 1, wherein said anterior optic comprises at least one biconvex gas lens.

4. The lens system of claim 1, wherein said soft material comprises silicone.

5. A method of treating macular degeneration, said method comprising implanting into the capsular bag of an eye of a patient a telescopic intraocular lens system comprising:
   a telescopic optical system comprising an anterior optic interconnected with a posterior optic, said optics substantially aligned on an optical axis of said optical system;
   wherein said optics are formed from a soft material and said optics are substantially immovable relative to each other along said optical axis in response to accommodative forces of the type observed in the capsular bag of the human eye.

6. A telescopic intraocular lens system comprising:
   a telescopic optical system comprising at least one gas lens element and at least one non-gas lens element, said lens elements substantially aligned on an optical axis of said optical system;
   wherein said optical system is sized to fit substantially within the capsular bag of the human eye.

7. The lens system of claim 6, wherein said optical system is 3 mm-6 mm long, as measured along said optical axis.

8. The lens system of claim 6, wherein said at least one non-gas lens element is formed from a soft material.

9. The lens system of claim 6, wherein said optical system, other than said at least one gas lens element, is formed from a soft material.

10. The lens system of claim 6, wherein said optical system comprises at least one pair of biconvex gas lenses.

11. The lens system of claim 10, wherein said optical system further comprises at least one pair of biconcave gas lenses posterior of said biconvex gas lenses.

12. A method of treating macular degeneration, said method comprising implanting the lens system of claim 6 into the capsular bag of an eye of a patient.

\* \* \* \* \*